(12) United States Patent
Nomoto et al.

(10) Patent No.: US 6,887,507 B2
(45) Date of Patent: *May 3, 2005

(54) MEMBRANE STRUCTURE

(75) Inventors: Tsuyoshi Nomoto, Atsugi (JP); Yasuko Tomida, Atsugi (JP); Junji Ohyama, Yamato (JP); Tomoko Maruyama, Atsugi (JP)

(73) Assignee: Canon Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 515 days.

(21) Appl. No.: 09/455,546

(22) Filed: Dec. 7, 1999

(65) Prior Publication Data

US 2002/0155152 A1 Oct. 24, 2002

Related U.S. Application Data

(62) Division of application No. 08/824,258, filed on Mar. 26, 1997, now Pat. No. 6,019,998, which is a continuation of application No. 08/236,096, filed on May 2, 1994, now abandoned.

(30) Foreign Application Priority Data

May 18, 1993 (JP) ............................................. 5-115891
Mar. 31, 1994 (JP) ............................................. 6-063082

(51) Int. Cl.⁷ .............................................. A61K 9/127
(52) U.S. Cl. .................................. 426/450; 428/402.2
(58) Field of Search ............................ 424/450, 1.21, 424/9.321, 9.51, 417, 94.3; 428/402.2; 427/213.33, 213.34, 214; 210/632, 638, 690, 691, 500.27, 500.38

(56) References Cited

U.S. PATENT DOCUMENTS

| 4,798,740 A | 1/1989 | Tomida et al. ............. 427/43.1 |
| 4,840,821 A | 6/1989 | Miyazaki et al. ......... 427/430.1 |
| 4,921,757 A | 5/1990 | Wheatley et al. ......... 428/402.2 |
| 4,939,556 A | 7/1990 | Eguchi et al. ................. 357/4 |
| 4,957,851 A | 9/1990 | Tomida et al. .............. 430/272 |
| 4,990,291 A | 2/1991 | Schoen et al. ............... 264/4.7 |
| 5,041,224 A | 8/1991 | Ohyama et al. ........ 210/500.27 |
| 5,183,879 A | 2/1993 | Yuasa et al. ................ 528/503 |
| 5,260,002 A | 11/1993 | Wang ......................... 264/4.1 |
| 5,288,517 A | 2/1994 | Kanno et al. ............... 427/244 |
| 5,290,960 A | 3/1994 | Singh .......................... 554/79 |
| 5,491,093 A | 2/1996 | Yamamoto et al. ........... 436/71 |

FOREIGN PATENT DOCUMENTS

| JP | 5-7770 | 1/1973 |
| JP | 61-124384 | 6/1986 |
| WO | 89/08130 | 9/1989 |

OTHER PUBLICATIONS

E. Racker et al., "Reconstitution of Purple Membrane Vesicles Catalyzing Light–Driven Proton Up–Take and Adenosine Triphosphate Formation", J. Bio. Chem., vol. 249, No. 2, pp. 662–663 (1974).

E.E. Uzgiris et al., "Two–Dimensional Crystallization Technique for Imaging Macromolecules with Application to Antigen–Antibody–Complement Complexes", Nature, vol. 301, pp. 125–129 (1983).

R.B. Gennis, Biomembranes, Molecular Structure and Function, chapter 2, section 4, pp. 64–75.

(Continued)

Primary Examiner—Gollamudi S. Kishore
(74) Attorney, Agent, or Firm—Fitzpatrick, Cella, Harper & Scinto

(57) ABSTRACT

A membrane structure employing a structure in which a lipid membrane is held by a hydrophilic polymer. The hydrophilic polymer layer contains an aqueous phase. There are functional molecules distributed selectively throughout each layer. The membrane structure is adaptable to applications as a separating agent, filler or delivery agent by performing physical and chemical operations.

3 Claims, 6 Drawing Sheets

OTHER PUBLICATIONS

S. Nojima et al., ed., "Physical Properties of Liposome", Liposome, chapter 4, pp. 67–116.

R. Elbert et al., "Hydrophilic Spacer Groups in Polymerizable Lipids: Formation of Biomembrane Models from Bulk Polymerized Lipids", J. Am. Chem. Soc., vol. 107, pp. 4134–4141 (1985).

R. Neumann et al., "Peptide Liposomes from Amphiphilic Amino Acids", J. Am. Chem. Soc., vol. 108, pp. 487–490 (1986).

T. Kunitake et al., "Vesicles of Polymeric Bilayer and Monolayer Membranes", J. Am. Chem. Soc., vol. 103, pp. 5945–5947 (1981).

A. Laschewsky et al., "Self–Organization of Polymeric Lipids with Hydrophilic Spacers in Side Groups and Main Chain: Investigation in Monolayers and Multilayers", J. Am. Chem. Soc., vol. 109, pp. 788–796 (1987).

S.L. Regen, "Polymerized Liposomes", Liposomes: From Biophysics to Therapeutics, chapter 3, pp. 73–108 (1987).

Encyclopedia of Polymer Science and Engineering, vol. 17, "Vesicles", pp. 108–135 (1989).

J.H. Fendler et al., "Polymerized Surfactant Aggregates: Characterization and Utilization", Acc. Chem. Res., vol. 17, pp. 3–8 (1984).

MEMBRANE STRUCTURE

This application is a division of Ser. No. 08/824,258, filed on Mar. 26, 1997, now U.S. Pat. No. 6,019,998 which is a continuation of Ser. No. 08/236,096 filed on May 2, 1994 now abandoned.

BACKGROUND OF THE INVENTION

1. Field of the Invention

The present invention relates to a membrane structure to be applied as a separating agent or a filler or a delivery agent adaptable to a reactive element which performs physical or chemical operations as well as to various separating operations.

2. Related Background Art

Lipids are used as the component of an organism, and a phospholipid is, among the lipids, one of main components of a variety of membrane systems, such as the plasma membrane, the nuclear membrane, the mitochondrion membrane, the Golgi apparatus membrane, and the lysosome membrane, of a cell which forms an organism. Since the phospholipid is an amphipatic molecule having, in the molecule thereof, a hydrophilic group and a hydrophobic group, the water molecules are hydrated in the hydrophilic group and the hydrophobic group is removed from the environment of water if the phospholipid is suspended in a solution. As a result, the hydrophobic groups are aggregated to one another. The form of the aggregation differs depending upon the balance between the hydrophilic groups containing the hydrated water molecules and the hydrophobic groups and determines whether a micelle or a lipid bilayer membrane or a hexagonal structure is formed based on the form of the aggregation. Among the foregoing structures, the lipid bilayer membrane is the basic structure of an organic membrane. The lipid bilayer membrane can be used to artificially form a closed vacuole (liposome) including an aqueous phase. Further, enzyme and membrane-bound protein substance can be, components added to the bilayer membrane. Therefore, the bilayer membrane has been widely used as a model for analyzing the organic membrane, as to substance permeation and information transmission. Further, application to various functional elements has been anticipated. For example, a series of refined enzymes extracted from an organic membrane and embedded in a liposome membrane in order to analyze its function. The orientation with respect to the surface of the membrane is an advantageous means to analyze biological activity of a cell (for example, information receipt, energy conversion, active transportation and biosynthesis) which is a complicated membrane system involving a multiplicity of intracellular organelle. Actually, the fact that the energy conversion mechanism in a mitochondrial inner membrane conforms to a chemiosmotic hypothesis has been proven from an experiment using a model of conjugated reconstitution of bacteriorhodopsin and an ATP synthase (Racker, E. and Stoeckenius, W.: J. Biol. Chem., 249, 662–663 (1974)).

Further, engineered application of the foregoing reconstitution is exemplified by a technology using bacteriorhodopsin and disclosed in Japanese Patent Laid-Open No. 61-124384. That is, the foregoing system has a structure arranged in such a manner that refined bacteriorhodopsin extracted from halophile and the ATP synthase are held by a liposome membrane. By arbitrarily determining the outer and inner conditions of the liposome and by applying visible rays, the function of the bacteriorhodopsin held by the membrane causes protons to be transported from the aqueous phase on the outside of the liposome to that in the liposome. As a result, the electrochemical potential (membrane potential) of the proton is generated across the liposome membrane. By previously supplying ADP and inorganic phosphoric acid to the aqueous phase on the outside of the liposome, the ATP synthase allowed to coexist in the membrane is able to use the electrochemical potential to synthesize ATP from the ADP and the inorganic phosphoric acid. By disposing luciferase in the aqueous phase on the outside of the liposome, light can be emitted due to decomposition of luciferin using the synthesized ATP.

Since the liposome is able to hold a water soluble substance in the internal aqueous phase thereof, an application as a drag delivery capsule, such as a microcapsule, has been anticipated.

Another attempt has been made to develop a lipid membrane simulated to an organic membrane by, in an engineering manner, using the self-organizing characteristics of the lipid. The foregoing attempt is characterized by: membranes in each of which there is a monomolecular membrane of lipid (a Langmuir membrane: an L-membrane) developed on the interface between gas and liquid which are, as flat membranes, transferred onto a substrate where they are stacked (Langmuir-Blodgett film: LB film); a membrane (a black membrane: BLM) in which a bimolecular membrane of lipid is formed in each aperture formed in a partition plate disposed in a water solution; and a cast membrane. A suggestion has been made that a stable lipid membrane is, by the LB method, formed to have a flat structure by combining high molecular gel and a bimolecular membrane of lipid (refer to Japanese Patent Laid-Open No. 5-7770).

As a method of providing a desired physical or chemical function to the lipid membrane, a method can be used using functional lipid molecules as the component of the membrane and a method causing the functional molecules required to obtain a desired physical or chemical function to be held in the lipid membrane or on the lipid membrane. For example, it is exemplified by a structure formed by causing an organic metal complex (ferrocene, a ruthenium complex or a phthalocyanine complex) or a functional pigment (a squallyrium derivative) having a synodic body forming ability to be held in the membrane or a structure using an amphipathic compound or a high molecular compound having a plurality of functional groups of atoms as the material of the membrane.

As an example of developed organic functional elements using a protein substance, an attempt has been made to arrange functional molecules to be stacked in 3D manner by introducing, into the monomolecular membrane of lipid, a ligand capable of singularly bonding with a protein substance (Refer to Uzgiris, E. E., Krongrg, R. D.: Nature, 301, 125–129 (1983)).

Another attempt has been made which has an arrangement that particles having lipid membrane layer formed on the carrier thereof are used to separate the organic substance (refer to Japanese Patent Laid-Open No. 3-502836).

The high standard function of an organism is achieved by cooperation of plural kinds of enzymes. A conventional lipid membrane has been used only as the field for reconstituting hydrophobic enzymes among a multiplicity of enzymes of an organism that can be carried by the membrane. To apply the high standard functions of an organism in an engineering manner, a structure is required that links the function of the organic membrane and the function of the water soluble molecule. Furthermore, the organic membranes are differentiated depending upon their functions in a variety of systems (the plasma-membrane, the nuclear membrane, the mitochondrion membrane and the endoplasmic membrane). Moreover, the water soluble molecules included in the membrane system differ depending upon the type and the concentration. The foregoing fact is an important factor to prevent feedback inhibition in the multi-stage enzyme reaction to cause the reactions to proceed as desired. Therefore, the simulation system of the functions of an organism must have a structure arranged such that the functional molecules are individually sectioned with adequate concentrations. From the foregoing, problems experienced with the conventional structures are as follows.

Liposome presents a problem in that membranes having different components cannot be stacked. What is worse, the membrane suffers from unsatisfactory strength, causing a problem to arise in that a large area membrane cannot easily be formed.

A flat membrane of a type manufactured by the LB method as disclosed in Japanese Patent Laid-Open No. 5-7770 exhibits a capability of forming a large area membrane but lacks the fluidity of the membrane. This is because the mutual reactions due to the diffusion and collision of molecules in the membrane surface have been interrupted. Since the foregoing flat membrane is a secured membrane, another problem arises in that the mutual reactions of molecules held in the individual membrane surfaces have been interrupted. Since the lipid bilayer membrane manufactured by the LB method is formed into a flat shape, the number of types of the lipid membranes that are able to co-exist in one water solution must be two or less.

SUMMARY OF THE INVENTION

An object of the present invention is directed to overcome the foregoing problems experienced with the conventional membrane structure, and therefore an object of the invention is to provide a membrane structure using a lipid membrane and exhibiting a great advantage in terms of widening the applicable range.

According to one aspect of the invention, there is provided a membrane structure comprising: one or more structures in each of which a lipid layer is held by a hydrophilic polymer layer which contains an aqueous phase, wherein one or more lipid layers form a spherical surface.

According to a further aspect of the present invention, a membrane structure comprising one or more structures wherein in each of said structures a lipid layer is held by a hydrophilic polymer layer having an aqueous phase, wherein a spherical surface is formed in each of said lipid layers According to yet another aspect of the present invention, a membrane structure comprising one or more structures wherein in each of said structures a lipid layer is held by a hydrophilic polymer layer having an aqueous phase, wherein a spherical surface is formed in each of said lipid layers held by said hydrophilic polymer, and wherein each layer is formed into a spherical shape.

According to yet a further aspect of the present invention, a membrane structure comprising one or more structures wherein in each of said structures a lipid layer is held by a hydrophilic polymer layer having an aqueous phase, wherein a spherical surface is formed in each of said lipid layers held by said hydrophilic polymer, and wherein the structure is arranged in such a manner that so that particles formed by covering the outer surface of a spherical hydrophilic polymer layer with a lipid layer and disposed in said hydrophilic polymer layer.

Other and further objects, features and advantages of the invention will be appear more fully from the following description.

BRIEF DESCRIPTION OF THE DRAWINGS

FIGS. 3A and 3B are views which illustrate the membrane structure according to the present invention and formed on the outer wall of a cylindrical base, wherein FIG. 3A is a perspective view which illustrates an end in a cross sectional, and FIG. 3B is a cross sectional view taken in a direction passing the central axis and perpendicular to the axis;

DESCRIPTION OF THE PREFERRED EMBODIMENT

Figure 1A:
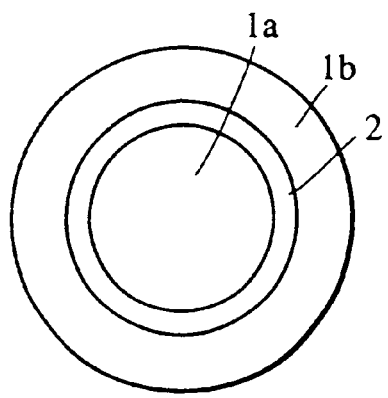
FIGS. 1A and 1B are cross sectional views which illustrate an example of the structure of a spherical membrane structure according to the present invention.
Figure 1B:
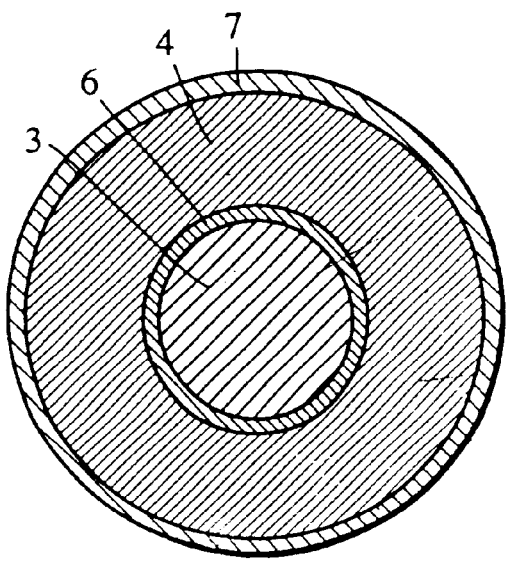

The structure and the shape of a membrane structure according to the present invention are selected depending upon the object. For instance, an example of a spherical structure is illustrated in FIG. 1 which is a cross sectional view passing through the center of the sphere. FIG. 1A illustrates a structure in which hydrophilic polymer layers 1a and 1b including an aqueous phase (hereinafter called simply a "hydrophilic polymer layer) hold a lipid membrane layer 2. FIG. 1B illustrates a structure in which hydrophilic polymer layers 3 and 4 hold a lipid layer 6 and the outer surface is covered with a lipid layer 7. Each of the foregoing layers forming the foregoing structures is a spherical layer which constitute a spherical surface, each layer forming a concentric spherical surface. Another structure shown in FIG. 2 may be employed in which a plurality of spheres are enclosed in one sphere.

Figure 3A:
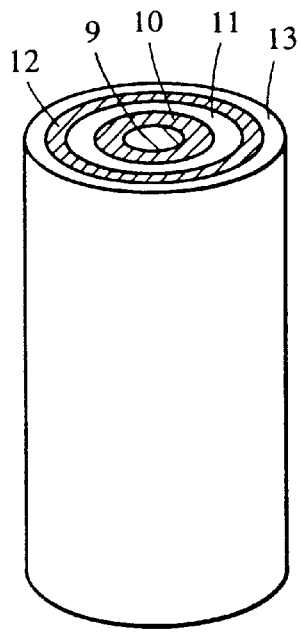
Figure 3B:
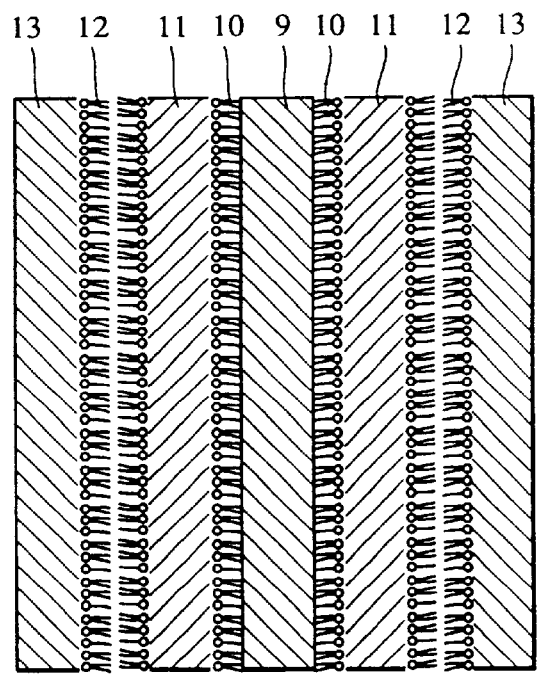

By forming the membrane structure by using a base, a membrane structure formed into a shape corresponding to the base can be obtained. FIGS. 3A and 3B illustrate a structure in which hydrophilic polymer layers 11, 13, lipid membrane layers 10 and 12 are alternately stacked on the outer wall of a cylindrical base 9.

Figure 4A:
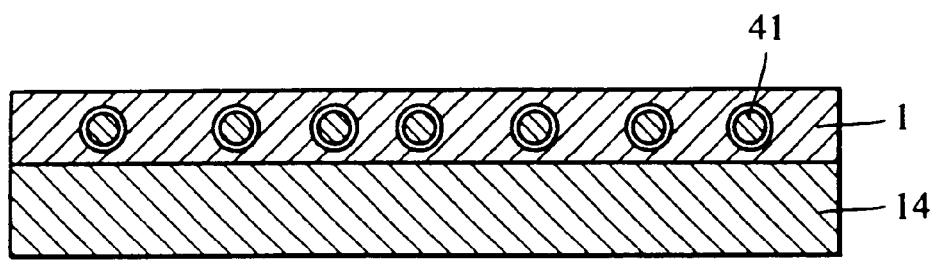
FIGS. 4A and 4B are cross sectional views which illustrate an example of a structure of the membrane structure of the present invention formed by combining a plane membrane and a spherical membrane structure.
Figure 4B:
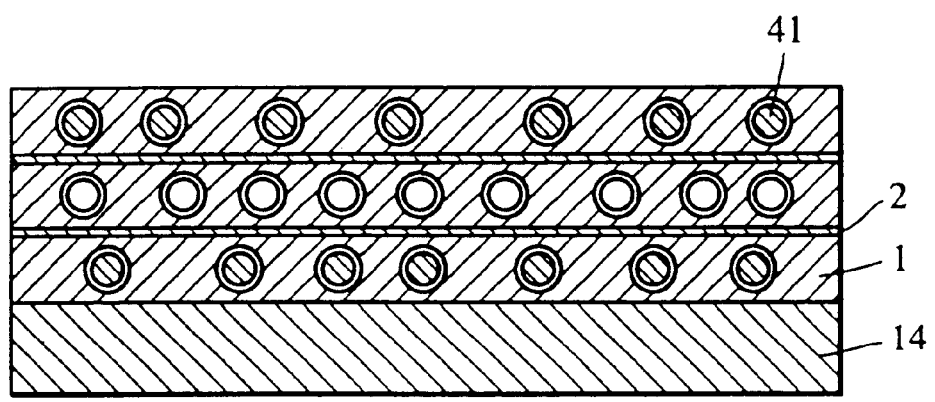

Another structure as shown in FIGS. 4A and 4B may be employed in which a multiplicity of spherical membrane structures 41 are dispersed in a plane layer (hydrophilic polymer layer 1). The spherical structures may be selected from a variety of structures exemplified by those shown in FIGS. 1 and 2.

Figure 2:
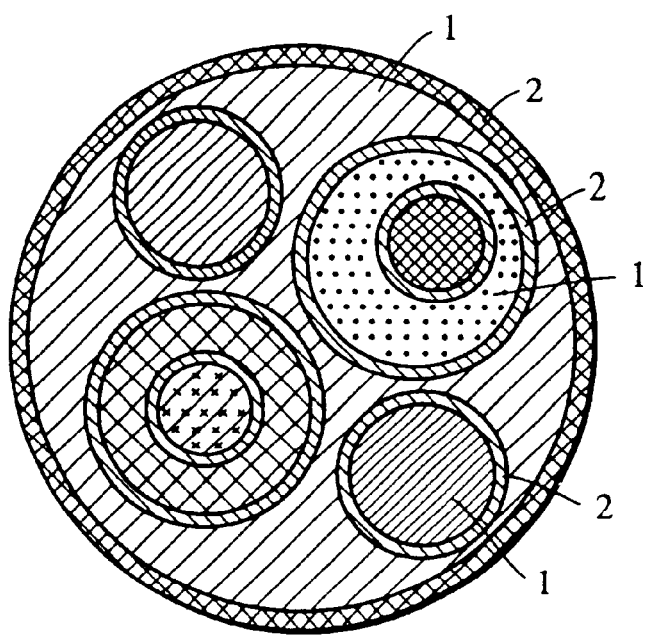
FIG. 2 is a cross sectional view which illustrates another structure of the spherical membrane structure according to the present invention.

A plurality of the hydrophilic polymer layers of the membrane structure according to the present invention may have the same or different thickness and composition. In a case where a plurality of lipid membrane layers are formed, the same arrangement may be employed. Other structures arranged as shown in FIGS. 1B and 2 may be employed in which the lipid membrane layer is formed on the outer surface.

The hydrophilic polymer layer and the lipid layer in the membrane structure according to the present invention may be cross linked if necessary. The subject layers to be cross linked are selected in accordance with the object or the compositions of the layers. By cross linking the hydrophilic polymer layer and the lipid membrane layer as described above, the membrane structure can be stabilized.

The lipid membrane layer of the membrane structure according to the present invention have a structure adaptable to a desired purpose. It is preferable that a lipid membrane contain amphiphatic lipid molecules as the basic component thereof. The amphiphatic lipid molecular membrane may be a monolayer membrane or a bilayer membrane. The lipid for forming the lipid membrane may be selected from a variety of substances known as amphiphatic substances, as for example, phospholipid, such as phosphatidyl choline, phosphatidyl serine, phosphatidyl ethanol amine, N-methyl phosphatidyl ethanol amine, N,N-dimethyl phosphatidyl ethanol amine, phosphatidic acid, phosphatidyl inositol or phosphatidyl glycerol, or corresponding lysophospholipid or a variety of fatty acids.

The lateral diffusion of the lipid molecules in the lipid bilayer, that is, the fluidity of the lipid membrane is defined in accordance with the state of its phase in such a manner that the lipid membrane is fluid if the phase is the liquid phase and the fluidity is losting in a gel phase. If functional molecules are contained in the lipid membrane and is intended to efficiently obtain the functions by using their lateral diffusion and collision in the membrane, the lipid bilayer membrane must be in the liquid phase at temperatures corresponding to the temperature range for use.

The thermodynamics concerning the phase transition phenomenon of the lipid has been disclosed in "Biomembranes; Molecular Structure and Function" authored by Robert B. Gennis, published by Shpringer Farelark Tokyo, pp. 64 to 75) and "Liposome" edited by Shoushichi Nojima, Junzo Sunamoto and Keizo Inoue, published by Nankodo, chapter 4). Also the temperature, at which the transition of a mixture lipid from the gel phase to the liquid phase takes place, can be determined experimentally in accordance with a DSC (Differential Scanning Calorimeter) or the like in such a manner that combinations of the thermodynamic parameters described in the foregoing disclosures are considered.

The introduction of the cross linking structure between the lipid membrane layer and the hydrophilic polymer layer improves the stability of the lipid membrane layer as described above. However, it decreases the fluidity of the lipid membrane. Therefore, it is preferable that the ratio of the lipid membrane layer and the hydrophilic polymer be varied in accordance with the object. If the hydrophilic polymer encounters a phase transition close to the transition temperature for the phase of the lipid or close to the temperature of use, the volume change of the hydrophilic polymer breaks the lipid membrane layer. Therefore, a suitable combination of the lipid and the hydrophilic polymer layer must be selected in accordance with the appropriate phase transition temperature.

The hydrophilic polymer layer of the membrane structure according to the present invention is formed adjacent to the lipid membrane layer. A hydrophilic polymer layer can be formed by a method comprising the steps of polymerizing monomers for forming the hydrophilic polymer and, if necessary, performing the cross linking or a method comprising the step of cross linking a water-soluble hydrophilic polymer. In the foregoing case, a polymer layer containing an aqueous phase can be obtained. The monomers for forming the hydrophilic polymer are exemplified by an acidic monomer, such as styrenesulfonic acid, acrylic acid or methacrylic acid, a basic monomer, such as dimethyl aminoethyl methacrylate or 2-hydroxy-3-methyloxypropyl trimethyl ammonium chloride, polysaccharide, such as alginic acid, a water soluble polymer, such as polypeptide exemplified by fibrin or collagen, and their mixtures.

A polymerization starting material for use in a case where the monomers are polymerized by radical polymerization is selected in accordance with the type of the employed monomer. For example, dibenzoyl peroxide, azobisisobutyronitrile, nitryl peroxide, acetyl peroxide or persulfate may be employed. Light radical polymerization may be performed by using a photosensitizer, such as riboflavin. The hydrophilic polymer layer can be obtained by cross linking a polysaccharide, such as alginic acid, in the presence of calcium ions or magnesium ions.

Also in the hydrophilic polymer layer, adjustment of the ratio of the aqueous phase or the degree of polymerization or the degree of cross linking will give mobility to the contained substances in the layer so as to improve the efficiency in the reactions.

The ratio of the aqueous phase contained in the hydrophilic polymer layer can be adjusted by selecting the concentration of the monomer at the time of performing the polymerization. The thickness of the layer and the degree of polymerization of the polymer for forming the layer can be adjusted by adding an agent for delaying the polymer reactions or an inhibiting agent or by stopping light irradiation in a case of light polymerization. The agent for inhibiting the radical polymerization is, depending upon the type of the employed monomer, exemplified by hydroquinone sodium sulfonate, sodium ascorbate, 2,2,5,5-tetramethyl pyrrolidine-1-oxyl-3-sodium carboxylate, 2,2,5,5-tetramethyl pyrroline-N-oxide-3-sodium carboxylate, iron chloride, copper chloride, zinc chloride and potassium ferrocyanide.

In the case where the cross linking structure is formed between the lipid membrane layer and the hydrophilic polymer layer, a known cross linking method for use in the chemical modification field of protein substances may be employed. For example, cross linking reactions can be allowed to proceed between a carboxylic group and an amino group or a hydroxyl group by using a reagent, such as carbodiimide, which is capable of forming a cross linking structure between the foregoing groups in accordance with dehydration condensation. By using the foregoing reagent, a portion obtainable from a monomer of a type having a carboxylic group, such as acrylic acid or methacrylic acid, and the amphiphatic compound having an amino group, such as phosphatidyl ethanol amine can be cross linked. Similarly, a portion obtainable from acrylamide and the fatty acid can be cross linked, and a portion obtainable from acrylamide and phosphatidyl serine can be cross linked. The cross linking reactions allowed to proceed between the amino group and thiol can be performed by using a reagent, such as N-succinimidyl-3-(2-pyridylditio) propionate. By using a reagent of the foregoing type, a peptide polymer having a thiol group and a amphiphatic compound having an amino group can be cross linked for example.

An example of a method of manufacturing the membrane structure according to the present invention will now be described. Initially, the water soluble monomer for forming the hydrophilic polymer layer, the amphiphatic compound for forming the lipid membrane, water and an organic solvent are combined to form a water-in-oil type emulsion. The monolayer membrane of the amphiphatic compound is oriented on the surface of water particle containing the water soluble monomer in such a manner that the hydrophilic portion faces the aqueous phase in the particle and the hydrophobic portion faces the organic solvent phase (the oil phase) outside the particle. By using a substance obtained by cross linking the water soluble monomer on the amphiphatic compound if necessary, the polymerization reactions of the monomer cross linked on the amphiphatic compound and the monomer contained in the aqueous phase enable a cross linked structure to be formed between a hydrophilic polymer layer formed in the particle and a membrane layer formed from the amphiphatic compound. That is, the monolayer membrane of the amphiphatic compound is partially fixed to the amphiphatic polymer layer due to cross linking when the water soluble monomers in the particle are polymerized. As a result, spherical membrane particles can be obtained, the hydrophilic polymer layer of being covered with the monolayer membrane of the amphiphatic compound which maintains fluidity in inverse proportion to the degree of cross linking. It should be noted that the method of polymerizing the water soluble monomer in the particles is selected depending upon the type of the employed monomer.

The organic solvent for forming the oil phase may be a water insoluble solvent exemplified by an aliphatic hydrocarbon solvent (n-hexane or benzene), aromatic solvent (benzene, xylene or toluene), chloroform or carbon tetrachloride. The organic solvent is not limited particularly if the employed solvent is able to form the single molecular membrane of the amphiphatic compound for forming the lipid membrane on the interface with water.

Although the thus-obtained spherical membrane particles are not stable in water because the particles are in the form in which the hydrophobic portion of the amphiphatic compound projects over the surface thereof, the particles can be stably dispersed in a solvent having a low polarity, such as diethylene glycol, formamide, acetonitryl or cyclohexane or a solution containing a surface active agent, as for example, sodium cholate, β-D-octylglucoside, CHAPS (3-[(3-cholamidopropyl)dimethylammonio]-1-propanesulfonate), TWEEN (polyoxyethyleneglycolsorbitane alkyl ester) or TRITON X-100 (polyoxyethyleneglycol p-t-octylphenyl ether). The concentration of the low polarity solvent or the surface active agent is determined in accordance with the structure of the spherical membrane particles and the degree of cross linking between the monolayer membrane of the amphiphatic compound and the hydrophilic polymer layer. By dispersing the spherical membrane particles in the low polarity solvent or the solution containing the surface active agent and by adding the amphiphatic compound to raise the polarity of the solvent or to lower the concentration of the surface active agent, the molecules of the amphiphatic compound added later are allowed to adhere in such a manner that its hydrophobic portion is oriented toward the surface of the spherical membrane particle so that the lipid membrane layer composed of the bilayer lipid membrane is formed on the surface. The form of the amphiphatic compound to be added later to the aqueous phase in which the spherical membrane particles are dispersed is formed into an inverted micelle if the low polarity solvent is used or formed into a micelle if the surface active agent is used. As a means for raising the polarity of the solvent, an antiphase evaporation method or the like is employed. As a means for lowering the concentration of the surface active agent, a dilution method, a dialysis method or a gel filtering method may be employed. The quantity of the amphiphatic compound to be added later must be sufficient to form the lipid bilayer membrane. If the quantity is too large, a problem of forming liposome arises or a problem in that the lipid membrane is undesirably formed into multiple layers. The removal of undesired liposome can be performed by, for example, a density-gradient centrifugation and fractionation method or a gel filtration method. By having coexisting functional molecules having desired membrane bonding characteristics at the time of forming the lipid bilayer membrane, the functional molecules can be held by the lipid layer. Further, the composition of the lipid membrane layer can be changed between the inner layer and the outer layer of the bilayer membrane. A substance which can be cross linked on the monomer for forming the hydrophilic polymer layer to be stacked on the lipid membrane layer may be added to the amphiphatic compound.

Then, the hydrophilic polymer layer is further stacked on the surface layer of the spherical membrane particle, the surface layer being made of the lipid membrane layer composed of the lipid bilayer membrane. The second hydrophilic polymer layer can be stacked by a method comprising the steps of, for example, of enclosing a polymerization initiating agent or a sensitizer for starting the light polymerization into the spherical membrane particles, dispersing the enclosure substance in a solvent containing the water soluble monomer for forming the hydrophilic polymer molecular layer, leaking the polymerization initiating agent or the sensitizer for starting the light polymerization which has been enclosed in the spherical membrane particles to the outside of the spherical membrane particles, and, if necessary, applying light to perform isotropic polymerization on the outer surface of the spherical membrane particles.

The enclosure of the polymerization initiating agent or the like into the spherical membrane particles or leaking of the same from the spherical membrane particles can be performed by using the phase transition of the lipid membrane layer occurring due to the temperature condition. That is, since the permeability of the lipid bilayer membrane with respect to a low molecular substance becomes maximum at a temperature close to the phase transition temperature, raising the spherical membrane particles to the phase transition temperature while dispersing the same in the solvent containing the reagent for initiating the polymerization reaction will enable the reagent to penetrate into the spherical membrane particles. After the reagent has been penetrated, the temperature of the spherical membrane particles is changed to a level at which the membrane permeability is low, and the reagent can be enclosed in the spherical membrane particles. When the temperature of the spherical membrane particles is again changed to a level close to the phase transition temperature, the membrane permeability of the enclosed reagent can be obtained. Therefore, the reagent can be leaked from the spherical membrane particles, and accordingly addition of the water soluble monomer to the outer aqueous layer will form the isotropic polymer layer on the outer wall of the spherical membrane particles.

When the polymerization reaction is stopped at an appropriate moment, a layer having a desired thickness can be formed in the hydrophilic polymer layer on the lipid membrane layer. The hydrophilic polymer layer can be held by the functional molecules by mixing the functional molecules in the water soluble monomer. When the component of the outer layer of the formed lipid membrane layer is a substance in which the water soluble monomer is cross linked for forming the hydrophilic polymer layer, the cross linked structure can be formed between the lipid membrane layer and the hydrophilic polymer layer.

In order to alternately stack the lipid membrane layers and the hydrophilic polymer layers on the surface layer of the thus-obtained spherical membrane particles, the foregoing process must be repeated. The composition in each layer can be changed at the time of stacking the layers.

Then, a process for forming the membrane structure according to the present invention on the base will now be described. The base to be employed is selected in accordance with the purpose of the obtained membrane structure. If the membrane structure must have physical strength, the base is made of a material selected from a group consisting of an inorganic material, such as glass, mica, plastic exemplified by polyvinyl chloride, silicon or a polymer material or fiber, such as hollow thread. If the membrane structure must have electric functions, the base is made of a conductor, such as metal, graphite or a semiconductor, or a chemical modified electrode or an electrode covered with a polymer material.

Since the hydrophilic characteristics (hydrophobic characteristics) of the surface of the base influences the stacked structure, it is preferable that the characteristics of the surface of the base be adjusted to meet the desired object. If the surface of the base has the hydrophilic characteristics, the hydrophilic polymer layer or the lipid membrane layer having the hydrophilic portion oriented toward the surface of the base is formed on the surface of the base. If the surface of the base has the hydrophobic characteristics, a lipid membrane layer having a hydrophobic portion oriented toward the surface of the base is formed on the surface of the base.

The procedure for forming the membrane structure according to the present invention on the base is basically the same as that for forming the spherical membrane structure. If the monomers for forming the hydrophilic polymer layer are polymerized on the base to form the hydrophilic polymer layer and then it is immersed in the organic solvent containing the amphiphatic compound for forming the lipid membrane layer, a lipid monolayer membrane is, on the top surface of the hydrophilic polymer layer on the base, so that the amphiphatic compound has its hydrophilic portion oriented toward the surface of the hydrophilic polymer layer. By adding, as the amphiphatic compound, a substance having a structure that can be cross linked with the hydrophilic polymer layer formed previously, a cross linked structure can be formed between the hydrophilic polymer layer and the lipid membrane layer. Then, a method similar to that described above is employed to form the bilayer membrane of the lipid, the hydrophilic polymer layer and the lipid membrane layer so that a desired number of membrane structures can be obtained.

By causing a medicine, or functional molecules for a specific object or reactive element for use in the reaction, to which the functional molecules relate, to be held in a predetermined layer of the membrane structure according to the present invention, the membrane structure according to the present invention can be applied as a reactive element for performing physical chemistry reactions in a variety of display devices, as a separating agent, as a filler, as a delivery agent applicable to a DDS (Drug Delivery System), or as a converting agent or a bioreactor. The functional molecule is exemplified by an enzyme concerning, for example, biochemical catalytic reaction, optical response, streoscopic molecule recognition reaction, electron transmission reaction, membrane fusing reaction, nucleic acid, pigment and functional organic compound.

EXAMPLES

Examples of the present invention will now be described in detail. Fluids A to E according to the following examples are composed as follows. The lipid is in the form of a mixed system which contains unsaturated phosphatidyl choline as the main component and phosphatidyl ethanol amine, phosphatidyl serine and cholesterol, the lipid having a gel/liquid phase transition temperature (Tc) of 5° C. The hydrophilic polymer layer to be formed in the following examples is formed into a gel layer containing an aqueous phase.

Fluid A:

A solution containing 7 wt % acrylamide, 1.75 wt % N,N'-methylene bisacrylamide and N,N,N',N'-tetramethyl ethylene diaimne (TEMED) at a ratio of 1.25 μl/ml.

Fluid B:

A solution obtained by dissolving lipid in a mixture solvent of toluene and chloroform (a volume ratio of 7:3) at a ratio of 25 mg/1.5 ml.

Fluid C:

A solution obtained by adding, to Fluid B, phosphatidyl serine formed by cross linking acrylamide with 1-ethyl-3-(3-dimethyl amino propyl) carbodiimide (EDC manufactured by PIERCE), the phospatidyl serine being added in a quantity of 10 wt %.

Fluid D:

A solution obtained by adding, by 20 wt %, myristic acid prepared by cross linking acrylamide monomer with EDC to Fluid B.

Fluid E:

A solution obtained by uniformly dispersing lipid in a mixture solvent of water and diethyl ether at a ratio of 1:3 (volume ratio) at a concentration of 25 mg/1.5 ml.

The light irradiation was performed in such a manner that white fluorescent lamps (four 6 W lamps) were disposed at a distance of about 10 cm to uniformly irradiate the subject.

Example 1

Fluid C was mixed with a solution obtained by adding riboflavin to Fluid A at a ratio of 0.35 mg/ml, so that water-in-oil (W/O) type emulsion was obtained. The emulsion was irradiated with white fluorescent lamps (four 6 W lamps) disposed at a distance of about 10 cm to polymerize and gel acrylamide in the particle aqueous phase. Spherical particles (gel sphere) in the form having a gel layer covered with a lipid monolayer membrane was obtained. The polymerization reactions were completed in about 20 minutes. A gel sphere dispersed solution was diluted with toluene and subjected to a centrifugal separation to recover the gel sphere. The dispersion into the toluene and the recovery by the centrifugal separation were repeated so that excessive lipid that had not been oriented to the interface between water and organic solvent was removed. Then, the gel sphere was dispersed in Fluid E and allowed to stand at room temperature, so that diethyl ether was slowly removed by evaporation. Thus, the monolayer membrane of lipid on the surface of the gel sphere was formed into bilayer membrane. A density gradient centrifugation method using sucrose was employed to recover the gel sphere having the surface formed into the lipid bilayer membrane. It was dispersed in pure water to measure the particle size by a light scattering method, resulting in an average particle size of 830 nm.

Then, the gel sphere was added to 0.7 mg/ml riboflavin solution and allowed to stand in a dark place at a phase transition temperature of 5° C. After it was allowed to stand for 3 hours, the temperature was raised to 25° C., so that riboflavin was enclosed in the gel sphere. The riboflavin dispersed solution was diluted with water and the gel sphere was recovered by centrifugal separation. The dispersion into water and the centrifugal separation recovery were repeated, so that undesirable riboflavin was removed.

The recovered gel sphere was dispersed in Fluid A, and the system was shifted to the phase transition temperature in such a manner that it was irradiated with light (four 6W-white fluorescent lamps). The system was allowed to stand at the phase transition temperature for 15 minutes, and then it was diluted with water and subjected to centrifugal separation, so that the gel sphere was recovered. It was dispersed in pure water and the particle size was measured by a light scattering method, resulting in an average particle size of 1.56 μm.

The recovered gel sphere was suspended in water and mixed with Fluid C, so that a monolayer membrane of lipid was, as an emulsion, formed on the surface layer. The emulsion was diluted with toluene and subjected to centrifugal separation, so that the gel sphere was recovered. The dispersion into toluene and the centrifugal separation recovery were repeated, so that excessive lipid, that had not been oriented toward the surface of the gel sphere, was removed. Then, it was dispersed in Fluid E and allowed to stand at room temperature, so that diethyl ether was slowly removed by evaporation. Thus, the surface of the gel sphere was formed into the bilayer membrane of lipid. The gel sphere was recovered by a sucrose density gradient centrifugation method. It was dispersed in pure water and the particle size was measured by a light scattering method, resulting in 1.76 μm. The thus-obtained gel sphere was formed into spherical membrane structure in the form as shown in FIG. 1B in which, from the center toward the surface layer, a first hydrophilic polymer layer, a first lipid membrane layer, a second hydrophilic polymer layer and a second lipid membrane layer were stacked in this sequential order.

Example 2

A solution obtained by adding riboflavin to Fluid A at a ratio of 0.35 mg/ml and Fluid D was mixed, so that water-in-oil (W/O) type emulsion was obtained. The emulsion was irradiated with white fluorescent lamps (four 6 W lamps) to polymerize and gel acrylamide in the aqueous phase. As a result, spherical particles (gel sphere) in the form having a gel layer covered with a lipid monolayer membrane was obtained. A gel sphere dispersed solution was diluted with toluene and subjected to a centrifugal separation to recover the gel sphere. The dispersion into the toluene and the recovery by the centrifugal separation were repeated so that excessive lipid that had not been oriented to the interface between water and organic solvent was removed. Then, the gel sphere was added to and dispersed in a solution obtained by making lipid to be micelle in a water solution of 0.8% octyl glucoside (weight/volume), and then it was shifted to a dialysis tube to be dialyzed with respect to water at room temperature for 12 hours, so that the surface layer of the gel sphere was made to be a lipid bilayer membrane. A density gradient centrifugation method using sucrose was employed to recover the gel sphere having the surface formed into the bimolecular membrane. It was dispersed in pure water to measure the particle size by a light scattering method, resulting in an average particle size of 830 nm.

Then, the gel sphere was added to 0.7 mg/ml riboflavin solution and allowed to stand in a dark place at a phase transition temperature of 5° C. After it was allowed to stand for 3 hours, the temperature was raised to 25° C., so that riboflavin was enclosed in the gel sphere. The gel sphere dispersed solution was diluted with water and the gel sphere was recovered by centrifugal separation. The dispersion into water and the centrifugal separation recovery were repeated, so that undesirable riboflavin was removed.

The recovered gel sphere was dispersed in Fluid A, and the system was allowed to stand in ice water. After it was irradiated with light for 15 minutes, it was diluted with water, and subjected to centrifugal separation to recover the gel sphere. It was then dispersed in pure water and the particle size was measured by a light scattering method, resulting in an average particle size of 1.56 μm.

The recovered gel sphere was suspended in water and mixed with Fluid C, so that a monolayer membrane of lipid was, as an emulsion, formed on the surface layer. The emulsion was diluted with toluene and subjected to centrifugal separation, so that the gel sphere was recovered. The dispersion into toluene and the centrifugal separation recovery were repeated, so that excessive lipid, that had not been oriented toward the surface of the gel sphere, was removed. Then, the gel sphere was added to and dispersed in a solution obtained by making a lipid in the form of a micelle in a water solution of 0.8% octyl glucoside (weight/volume), and then it was shifted to a dialysis tube to be dialyzed with respect to water at room temperature for 12 hours, so that the surface layer of the gel sphere was made to be a bilayer membrane of lipid. It was dispersed in pure water to measure the particle size by a light scattering method, resulting in an average particle size of 1.82 μm. The thus-obtained gel sphere was formed into spherical membrane structure in the form as shown in FIG. 1B in which, from the center toward the outside, a first hydrophilic polymer layer, a first lipid membrane layer, a second hydrophilic polymer layer and a second lipid membrane layer were stacked in this sequential order.

Example 3

A solution obtained by adding riboflavin to Fluid A at a ratio of 0.37 mg/ml and Fluid C were mixed, so that an W/O type emulsion was obtained. It was then irradiated with light (four 6W-white fluorescent lamps, at a distance of 10 cm for 20 minutes) to polymerize acrylamide in the aqueous phase so as to gel it. As a result, spherical particles (gel sphere) comprising a gel layer covered with monolayer membrane of lipid were obtained. The gel sphere dispersed solution was diluted with toluene and subjected to centrifugal separation to recover the gel sphere. The dispersion into toluene and the centrifugal separation recovery were repeated so that excessive lipid that had not been oriented to the interface between water and the organic solvent was removed. Then, the gel sphere (wet weight of 1.0 g) was added to a solution (lipid content 1 mg/ml) in which lipid was made to be a micelle in 0.8% (weight/volume) octyl glucoside solution so that the gel sphere was dispersed. Then, 8.5 mg of bacteriorhodopsin made to be soluble by octyl glucoside was added to the dispersed solution, and it was shifted to a dialysis tube to be dialyzed at room temperature for 12 hours. As a result, the surface layer of the gel sphere was made to be a bilayer membrane of lipid and bacterio rhodopsin was re-constituted in the membrane. A sucrose density gradient centrifugation method was employed to recover the gel sphere having the surface which had been formed into the bilayer membrane of lipid. An adequate quantity of oxonol V (bis-[3-phenyl-5-oxoisoxazol-4-yl] pentamethineoxonol, which is an ethanol solution manufactured by Molecular Probes) was added so that the lipid membrane layer of the surface layer was fluorescent-indicated. It was then dispersed in pure water to measure the particle size by a light scattering method, resulting in an average particle size of 1.25 μm.

The gel sphere was added to 0.4 M calcium chloride solution and allowed to stand in a dark place at the phase transition temperature of 5° C. for 3 hours. After three hours had passed, the temperature was raised to 25° C., and it was diluted with water and subjected to centrifugal separation to recover the gel sphere. The dispersion into water and the centrifugal separation recovery were repeated, so that excessive calcium chloride was removed. Then, 10% sodium alginate (manufactured by Kibun Food Chemical) solution was added to the gel sphere and allowed to stand for 15 minutes in such a manner that it was stirred at a phase transition temperature. Then, it was diluted with water and subjected to centrifugal separation so that the gel sphere having the surface layer, on which a gel layer of alginate was formed, was recovered. It was then dispersed in pure water to measure the particle size by a light scattering method, resulting in an average particle size of 2.56 μm.

A solution obtained by diluting, with water to three times, a solution, in which riboflavin was dissolved in Fluid A at a concentration of 0.37 mg/ml, was prepared. Then, the gel sphere having the surface layer, which is the gel layer of alginate, was dispersed in the foregoing solution. It was allowed to stand in a dark place for 2 hours so that the solution on the outside of the gel sphere was allowed to penetrate the gel layer of the sodium alginate. The gel sphere was recovered by centrifugal separation, and it was immediately mixed with Fluid B to form an emulsion. Then, the emulsion was irradiated with light (four 6 W-white fluorescent lamps). It was diluted with toluene and subjected to centrifugal separation to recover the gel sphere. The dispersion into toluene and the centrifugal separation recovery were repeated so that excessive lipid, that has not been oriented, was removed. Then, the gel sphere was dissolved in a solution in which lipid was made to be micelle in 0.8% (weight/volume) octyl glucoside solution, and the dispersed solution was shifted to a dialysis tube to be dialyzed with respect to water at room temperature for 12 hours. As a result, the surface layer of the gel sphere was formed into a bilayer membrane of lipid. A sucrose density gradient centrifugation method was employed to recover the gel sphere having the surface layer formed into the bilayer membrane of lipid. It was dispersed in pure water to measure the particle size by a light scattering method, resulting in an average particle size of 2.82 μm. The bilayer membrane of lipid of the surface layer was fluorescent-indicated with $CC_6$ (1,1'-dihexyl-2,2'-oxacarbocyanide which is an ethanol solution manufactured by Molecular Probes) which is a fluorescent pigment having membrane potential sensitivity.

The thus-obtained gel sphere was formed into spherical membrane structure in the form as shown in FIG. 1B in which, from the center, a first hydrophilic polymer layer made of acrylamide gel, a first lipid membrane layer made of the bilayer membrane of lipid holding bacteriorhodopsin and indicated with oxonol V, a second hydrophilic polymer layer composed of a mixture layer of gel of alginate and acrylamide gel and a second lipid membrane layer formed by the bilayer membrane of lipid indicated with $CC_6$ were stacked in this sequential order.

The characteristics of the substance held in the membrane structure are as follows:

(1) First Lipid Membrane Layer:
  Bacteriorhodopsin: which is excited with 560 nm light to exhibit an ability of pumping proton.
  Oxonol V: which is excited with 580 nm to emit fluorescent light having the peak at 630 nm, the intensity of fluorescent light being changed in accordance with the potential of the membrane.

(2) Second Lipid Membrane Layer
  $CC_6$: which is excited with 460 nm light to emit fluorescent light having the peak at 505 nm, the intensity of fluorescent light being changed in accordance with the potential of the membrane.

Figure 5:
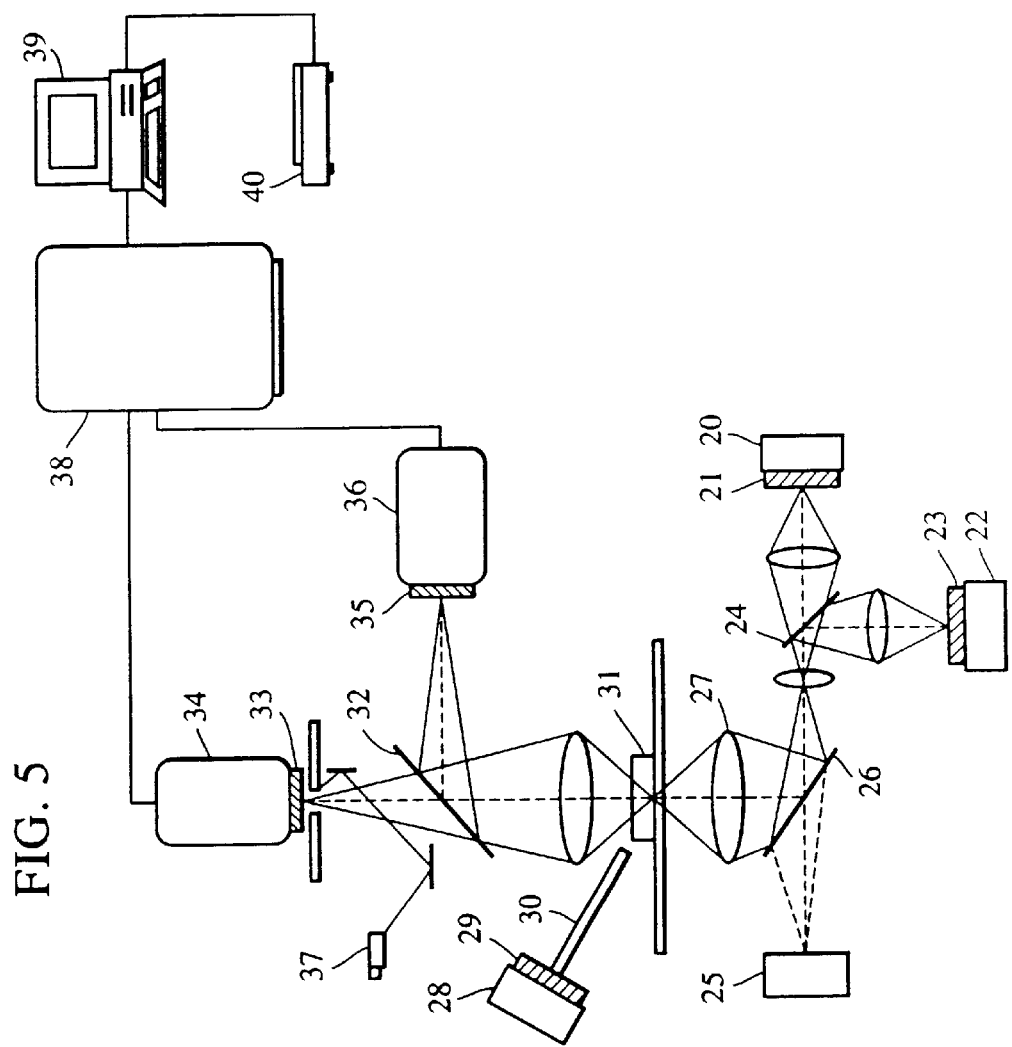
FIG. 5 is a schematic view which illustrates the structure of an apparatus for inspecting the membrane structure.

When the bacteriorhodopsin held by the first lipid membrane layer was excited so that protons are transported from the aqueous phase included in the outside second hydrophilic polymer layer to the aqueous phase included in the inside first hydrophilic polymer layer. As a result, the first hydrophilic polymer layer is made to be acid, while the second hydrophilic polymer layer is made to be alkaline. That is, a membrane potential is generated between the layers in such a manner that the first lipid membrane layer was interposed. Since the second hydrophilic polymer layer disposed on the inside of the second lipid membrane forming the surface layer is made to be alkaline, a membrane potential can be generated in the second lipid membrane. Since the oxonol V and $CC_6$, which are the is fluorescent pigments, the intensity of which is changed in accordance with the potential of the membrane, are held in the first and second lipid membranes, observation of the generation of the membrane potential taking place due to the effect of the proton pump under light applied to the amphiphatic as the change in the intensity of fluorescent light from the fluorescent pigment enables confirmation as to whether or not a desired structure has been formed in the obtained gel sphere. The confirmation was made by a measuring system arranged as shown in FIG. 5. The measuring system was constituted by using an optical microscope (BH-2 manufactured by Olympus).

A sample 31 in the measuring system shown in FIG. 5 was prepared by suspending 1 mg, the wet weight, of gel sphere in 0.1 ml of pure water to be set.

Light (580 nm) for exciting oxonol V is, from a light source 20, made incident upon the sample 31 through a monochromater 21, a dichroic mirror 24 (which reflects light shorter than a wavelength of 490 nm at an incidental angle of 45° and allows light longer than a wavelength of 490 nm at a maximum transmission ratio of 89% and which was manufactured by Nihon Shinku Kogaku), a full reflecting mirror 26 and a converging lens 27. Fluorescent light (630 nm) emitted from pigments excited by the exciting light is allowed to pass through a dichroic mirror 32 (which reflects light shorter than a wavelength of 520 nm at an incidental angle of 45° and allows light longer than a wavelength of 520 nm at a maximum transmission ratio of 89% and which was manufactured by Nihon Shinku Kogaku) to be made incident on an SIT camera (C2400-08 manufactured by Hamamatsu Photonics) 34 to which a short wavelength cut-off filter 33 (manufactured by Asahi Bunkosha and having a maximum transmission ratio of 88% and a cut-off wavelength of 590 nm) is attached, so that detection was performed.

On the other hand, light (460 nm) for exciting the pigment $CC_6$ is applied from a light source 22 to the sample through a monochromater 23 and the foregoing optical system. Fluorescent light (505 nm) emitted due to the foregoing operation is made incident upon an SIT camera (C2400-08 manufactured by Hamamatsu Photonics) 36 to which a band pass filter 35 (manufactured by Asahi Bunko and having a maximum transmission ratio of 88% and a transmission wavelength of 490 nm to 520 nm) is attached, so that detection was performed. In the foregoing state, the sample was, for 2 minutes, irradiated with 560 nm light for exciting bacteriorhodopsin emitted from a light source 28 through a monochromater 29 and a light guide 30. The change in the intensity of the fluorescent light is processed as two types of fluorescent light emission signals having different wavelengths and received by the two different SIT cameras, the process being made by an image processor 38 (ARGUS-50 manufactured by Hamamatsu Photonics). Obtained information was analyzed by a computer 39 (IBM/PC) to be transmitted to a printer 40 or the like as desired.

The position and focus adjustments of the sample 31 were performed in such a manner that light from the light source 25 is applied to a system formed by combining a phase difference condenser with the converging lens 27 and the light is detected through a binocular 37.

Figure 6:
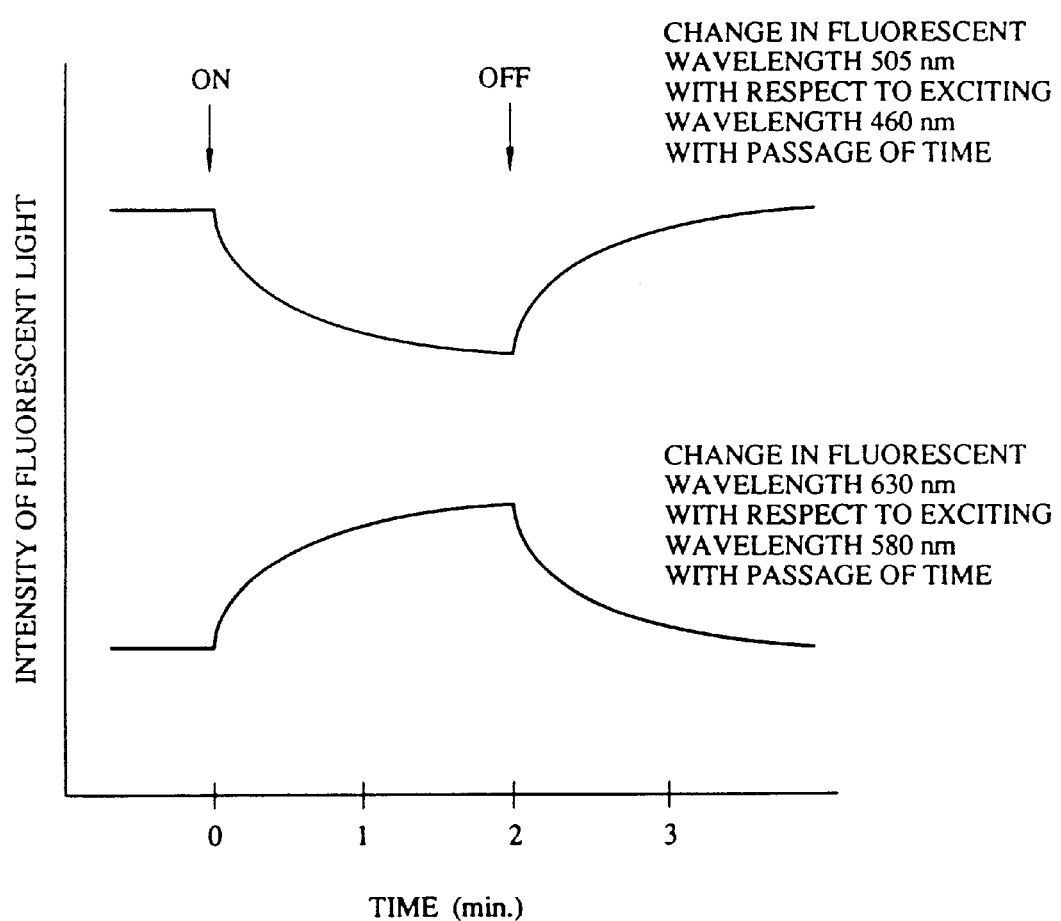
FIG. 6 is a graph which illustrates change in the intensity of fluorescent light realized in Example 3.

As shown in FIG. 6, the intensity of the fluorescent light of each pigment was changed at the start of the irradiation of 560 nm light. When the irradiation of 560 nm light was interrupted, the intensities were returned to the original state. That is, it was confirmed that the gel sphere obtained in this example has a desired structure and the membrane bonding substances can be selectively disposed in each lipid membrane layer.

Example 4

Riboflavin was added to Fluid A at a concentration of 0.35 mg/ml, and a solution containing 8-hydroxipyrene-1,3, 6-trisulfonic acid trisodium salt (manufactured by Funakoshi) in an adequate quantity as a first pH fluorescent indicator was prepared. Then, fluid C was mixed with the foregoing solution, so that an W/O type emulsion was obtained. The W/O type emulsion was irradiated with light (four 6W-white fluorescent lamps) to gel acrylamide in the aqueous phase, so that gel sphere having a gel layer covered with a lipid monolayer was obtained. The mixture solution was diluted with toluene and subjected to centrifugal separation to recover gel sphere. The foregoing dispersion into toluene and the centrifugal separation recovery were repeated to remove excessive lipid that had not been oriented to the interface between water and the organic solvent. Then, the gel sphere (wet weight of 1.0 g) was dispersed in a solution (lipid content of 1 mg/ml) in which lipid was made to be micelle with 0.8% (weight/volume) octyl glucoside solution, and bacteriorhodopsin (8.5 mg) was added. It was shifted to a dialysis tube to be dialyzed with respect to water at room temperature so that the monolayer membrane of lipid on the surface layer was made to be a bilayer membrane of lipid. Further, bacteriorhodopsin was re-constituted in the membrane. A sucrose density gradient centrifugation method was employed so that gel sphere having the surface layer made of the bilayer membrane of lipid was recovered. It was dispersed in pure water to measure the particle size by a light scattering method, resulting in an average particle size of 1.25 $\mu$m.

Then, the gel sphere was added to 0.4 M calcium chloride solution and allowed to stand in a dark place at the phase transition temperature of 5° C. for 3 hours. The temperature was raised to 25° C., and calcium chloride was enclosed in the gel layer under the bilayer membrane of lipid. It was diluted with water and subjected to centrifugal separation to recover the gel sphere. Further, the dispersion in water and the centrifugal separation recovery were repeated to remove excessive calcium chloride. Then, 10% sodium alginate solution and an adequate quantity of CARBOXY SNARF-X (manufactured by Funakoshi) as a second pH fluorescent indicator were added to the recovered gel sphere. The temperature of the mixture solution was maintained at 5° C., which was the phase transition temperature. While stirring the mixture solution, reactions were allowed to proceed for 15 minutes, and the mixture solution was diluted with water and subjected to centrifugal separation to recover the gel sphere. The recovered gel sphere was dispersed in pure water to measure the particle size by a light scattering method, resulting in an average particle size of 2.56 $\mu$m.

The gel sphere was dispersed in a diluted solution, in which riboflavin was added to Fluid A at a ratio of 0.35 mg/ml and CARBOXY SNARF-X was added in an adequate quantity and which was diluted with water to three times, the dispersed solution was allowed to stand in a dark place for 2 hours so that the components of the diluted solution was allowed to penetrate the surface gel layer. The gel sphere was recovered by centrifugal separation, and it was immediately dispersed in Fluid B to form an emulsion. Then, it was irradiated with light (four 6W-white fluorescent lamps). The dispersed solution was diluted with toluene and subjected to centrifugal separation to recover the gel sphere. Further, the dispersion in the toluene and the centrifugal separation recovery were repeated so that excessive lipid that had not been oriented was removed. The recovered gel sphere was dispersed in a solution in which lipid was made to be micelle in 0.8% (weight/volume) octyl glucoside solution. It was shifted to a dialysis tube to be dialyzed with respect to water at room temperature for 12 hours. As a result, the monolayer membrane of lipid in the surface layer was formed into a bilayer membrane. A sucrose density gradient centrifugation method was employed to recover the gel sphere having the surface layer made of the bilayer membrane of lipid. It was dispersed in pure water to measure the particle size by a light scattering method, resulting in that an average particle size of 2.82 $\mu$m.

The thus-obtained gel sphere was formed into spherical membrane structure in the form as shown in FIG. 1B in which, from the center, a first hydrophilic polymer layer made of acrylamide gel and indicated with the pH fluorescent indicator, a first lipid membrane layer made of the bilayer membrane of lipid holding bacteriorhodopsin, a second hydrophilic polymer layer composed of a mixture layer of gel of alginate and acrylamide gel and indicated with the second pH fluorescent indicator and a second lipid membrane layer formed by the bilayer membrane of lipid were stacked in this sequential order.

The characteristics of the substance held in the membrane structure are as follows:
(1) First Hydrophilic Polymer Layer:
   First pH Fluorescent Indicator: having a pKa of 7.8 to 7.9, a conjugate acid exciting wavelength of 400 nm, a conjugate basic exciting wavelength of 450 nm and a fluorescent wavelength of 515 nm in both acid and basic states.
(2) First Lipid Membrane Layer:
   Bacteriorhodopsin: which is excited with 560 nm light and which exhibits an ability of pumping protons.
(3) Second Hydrophilic Polymer Layer:
   Second pH Fluorescent Indicator: having a pKa of 7.8 to 7.9, conjugate acid exciting wavelengths of 529 nm and 569 nm, a conjugate acid fluorescent wavelength of 599 nm, a conjugate basic exciting wavelength of 587 nm and a conjugate basic fluorescent wavelength of 630 nm.

When the membrane structure is irradiated with visible light, the bacteriorhodopsin held in the first lipid membrane layer was excited. As a result, protons are transported from the aqueous phase included in the outside second hydrophilic polymer layer to the aqueous phase included in the inside first hydrophilic polymer layer. As a result, the first hydrophilic polymer layer was made to be acid, while the second hydrophilic polymer layer was made to be alkaline. Therefore, change in the pH takes place between the layers in such a manner that the first lipid membrane layer is interposed. Since the first and second hydrophilic polymer layers respectively contain pH fluorescent indicators having different exciting wavelengths and fluorescent wavelengths, measurements of the two types of fluorescent light beams generated due to the irradiation of the pH fluorescent indicator with light, a confirmation can be made that the membrane structure is formed into a desired structure.

Figure 7:
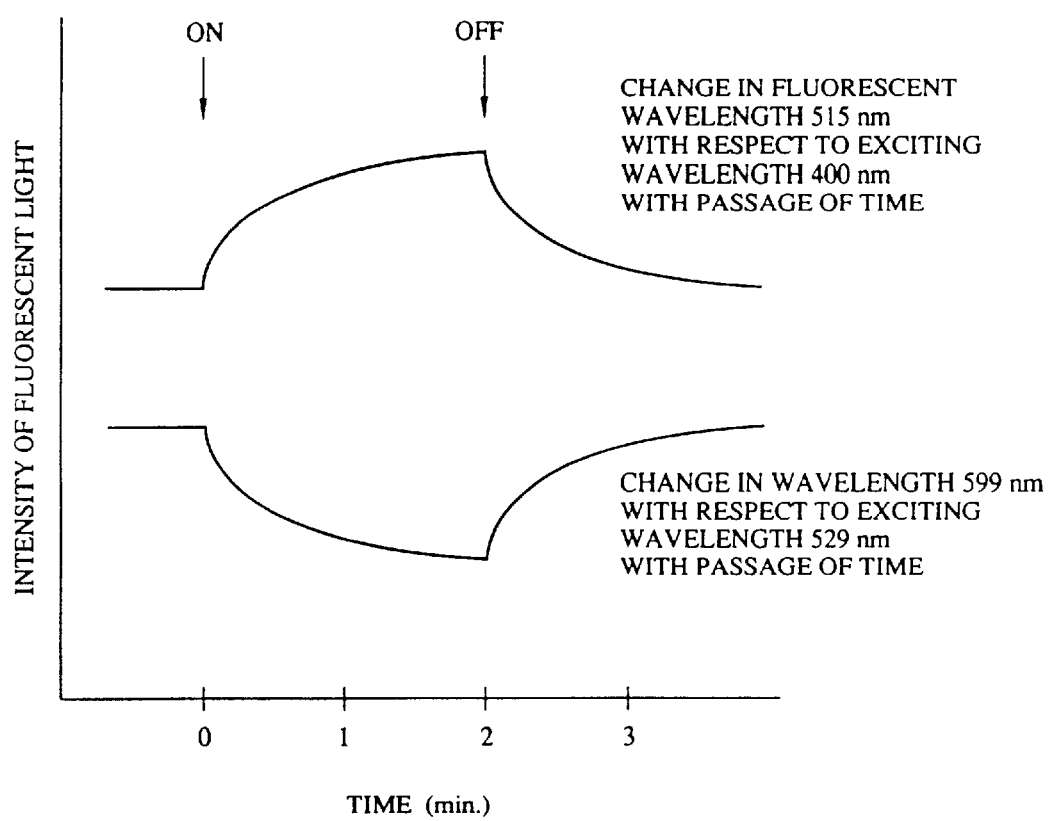
FIG. 7 is a graph which illustrates change in the intensity of fluorescent light realized in Example 4.

While employing the same method using the apparatus according to Example 3 shown in FIG. 5 except the exciting wavelength and the wavelength of fluorescent light adapted to the foregoing structure to irradiate the membrane structure according to this example with exciting light and to detect fluorescent light. Thus, results shown in FIG. 7 were obtained. That is, when bacteriorhodopsin is irradiated with exciting light in such a manner that exciting light for each pH fluorescent indicator is applied, fluorescent light peculiar to each pH fluorescent indicator indicating the pH change is emitted. When the light irradiation is stopped, the intensity of fluorescent light was restored to the original level. As a result, it was confirmed that the membrane structure according to this embodiment has a desired structure and desired substances can be selectively disposed in each layer.

The membrane structure according to the present invention employs the structure in which the lipid membrane layer is held by the hydrophilic polymer layer containing the aqueous phase. Therefore, desired functional molecules can be distributed and selectively disposed in each layer. Further, the concentration and so forth of the functional molecules and the like can be controlled as desired. As a result, employment of the membrane structure according to the present invention enables each stage in the multi-stage reaction in an organism to be separated and efficiently reconstituted in each region of the membrane structure.

If substances that react with the functional molecules held in the lipid membrane layer are contained in a layer adjacent to the lipid membrane layer, forming of the hydrophilic polymer layer enables the concentration of the reactive substances in the layer adjacent to the lipid membrane layer to be raised as compared with a case where an aqueous phase is formed adjacent to the lipid membrane layer. By adjusting the degree of polymerization of the hydrophilic polymer layer or the like, the diffusion ease and collision of the reactive substances in the layer can be maintained. Consequently, the reactions can be formed efficiently.

Although the invention has been described in its preferred form with a certain degree of particularly, it is understood that the present disclosure of the preferred form can be changed in the details of construction and the combination and arrangement of parts may be resorted to without departing from the spirit and the scope of the invention as hereinafter claimed.

What is claimed is:

1. A stacked membrane structure comprising:

a cylindrical base upon which said membrane structure is disposed, said membrane structure comprising hydrophilic polymer layers containing an aqueous phase and lipid membrane layers alternately stacked on an outer wall of the cylindrical base, thereby imparting a cylindrical shape to said membrane structure, wherein the compositions of two of the adjacent hydrophilic polymer layers, between which a lipid membrane layer is present, are different.

2. A stacked membrane structure comprising:

a cylindrical base upon which said membrane structure is disposed, said membrane structure comprising hydrophilic polymer layers containing an aqueous phase and lipid membrane layers alternately stacked on an outer wall of the cylindrical base, thereby imparting a cylindrical shape to said membrane structure, wherein the compositions of two of the adjacent lipid membrane layers, between which a hydrophilic polymer layer is present, are different.

3. A stacked membrane structure comprising:

a cylindrical base upon which said membrane structure is disposed, said membrane structure comprising hydrophilic polymer layers containing an aqueous phase and lipid membrane layers alternately stacked on an outer wall of the cylindrical base, thereby imparting a cylindrical shape to said membrane structure.

* * * * *

UNITED STATES PATENT AND TRADEMARK OFFICE
CERTIFICATE OF CORRECTION

PATENT NO. : 6,887,507 B2
DATED : May 3, 2005
INVENTOR(S) : Tsuyoshi Nomoto et al.

It is certified that error appears in the above-identified patent and that said Letters Patent is hereby corrected as shown below:

Title page,
Item [56], References Cited, FOREIGN PATENT DOCUMENTS,
"5-7770      1/1973" should read -- 5-7770      1/1993 --.

Column 3,
Line 50, "layers" should read -- layers. --;
Line 64, "that" (1st occurrence) should be deleted; and
Line 66, "and disposed" should read -- are disposed --.

Column 4,
Line 46, "constitute" should read -- constitutes --.

Column 5,
Line 12, "have" should read -- has --.

Column 10,
Line 1, "streoscopic" should read -- stereoscopic --;
Line 18, "diaimne" should read -- diamine --;
Line 25, "formed by cross linking acrylamide" should read
-- to which acrylamide was bonded --; and
Line 31, "prepared by cross linking acrylamide monomer" should read
-- to which acrylamide monomer was bonded --.

Column 12,
Line 61, "bacterio rhodopsin" should read -- bacteriorhodopsin --.

Column 14,
Line 64, "monochromater" should read -- monochromator --.

UNITED STATES PATENT AND TRADEMARK OFFICE
CERTIFICATE OF CORRECTION

PATENT NO. : 6,887,507 B2
DATED : May 3, 2005
INVENTOR(S) : Tsuyoshi Nomoto et al.

It is certified that error appears in the above-identified patent and that said Letters Patent is hereby corrected as shown below:

Column 15,
Line 7, "monochromater" should read -- monochromator --.

Signed and Sealed this

Fourteenth Day of February, 2006

JON W. DUDAS
*Director of the United States Patent and Trademark Office*